United States Patent
Chau et al.

(10) Patent No.: US 10,204,117 B2
(45) Date of Patent: Feb. 12, 2019

(54) RESEARCH PICTURE ARCHIVING COMMUNICATIONS SYSTEM

(71) Applicant: Synaptive Medical (Barbados) Inc., Bridgetown (BB)

(72) Inventors: Clinton Chau, Toronto (CA); Jonathan Resnick, Toronto (CA); Stewart Bright, Courtice (CA)

(73) Assignee: SYNAPTIVE MEDICAL (BARBADOS) INC., Bridgetown (BB)

( * ) Notice: Subject to any disclaimer, the term of this patent is extended or adjusted under 35 U.S.C. 154(b) by 374 days.

(21) Appl. No.: 14/891,026

(22) PCT Filed: Jun. 3, 2014

(86) PCT No.: PCT/CA2014/000482
§ 371 (c)(1),
(2) Date: Nov. 13, 2015

(87) PCT Pub. No.: WO2014/194406
PCT Pub. Date: Dec. 11, 2014

(65) Prior Publication Data
US 2016/0124949 A1  May 5, 2016

Related U.S. Application Data

(60) Provisional application No. 61/830,871, filed on Jun. 4, 2013.

(51) Int. Cl.
*G06F 17/30* (2006.01)
*G06F 19/00* (2018.01)
*G06T 1/00* (2006.01)

(52) U.S. Cl.
CPC ......... *G06F 17/3028* (2013.01); *G06F 17/30* (2013.01); *G06F 17/30073* (2013.01); *G06F 19/321* (2013.01); *G06T 1/00* (2013.01)

(58) Field of Classification Search
None
See application file for complete search history.

(56) References Cited

U.S. PATENT DOCUMENTS 6,272,470 B1   8/2001 Teshima
6,397,224 B1   5/2002 Zubeldia et al.
(Continued)

OTHER PUBLICATIONS

Tsui, G. K. W., & Chan, T. (2012). Automatic Selective Removal of Embedded Patient Information From Image Content of DICOM Files. American Journal of Roentgenology, 198(4), 769-772.
(Continued)

*Primary Examiner* — Son T Hoang
(74) *Attorney, Agent, or Firm* — Kagan Binder, PLLC (57) ABSTRACT

A system for de-identifying images and metadata containing personal information. A clinical subsystem connects to a clinical picture archiving and communication system (PACS) containing image data including metadata with personal information. The clinical subsystem includes an image data editor for de-identifying image data by deleting or altering the personal information in the image data according to instructions specified in a de-identification script. The de-identification subsystem includes an image metadata database and runs an edit script generator that can be used by a user to generate a de-identification script based on metadata stored in the image metadata database, without access to the associated image data.

13 Claims, 2 Drawing Sheets

(56) References Cited

U.S. PATENT DOCUMENTS

| | | | |
|---|---|---|---|
| 6,915,265 B1 | 7/2005 | Johnson | |
| 7,660,413 B2 | 2/2010 | Partovi et al. | |
| 8,031,920 B2 | 10/2011 | Brackett | |
| 8,326,849 B2 | 12/2012 | El Emam et al. | |
| 8,396,802 B2 | 3/2013 | Dala et al. | |
| 8,510,850 B2 | 8/2013 | Dove et al. | |
| 2003/0088771 A1 | 5/2003 | Merchen | |
| 2004/0078238 A1 | 4/2004 | Thomas et al. | |
| 2004/0168064 A1 | 8/2004 | Shimizu et al. | |
| 2004/0193901 A1* | 9/2004 | Bharara | G06F 19/321 713/193 |
| 2005/0165623 A1 | 7/2005 | Landi et al. | |
| 2006/0009692 A1 | 1/2006 | Fukuda | |
| 2006/0049936 A1* | 3/2006 | Collins, Jr. | A61B 5/1115 340/539.11 |
| 2007/0192140 A1* | 8/2007 | Gropper | G06F 19/322 705/3 |
| 2007/0255704 A1 | 11/2007 | Baek et al. | |
| 2008/0147554 A1 | 6/2008 | Stevens et al. | |
| 2009/0313170 A1* | 12/2009 | Goldner | G06F 19/363 705/50 |
| 2011/0110568 A1 | 5/2011 | Vesper et al. | |
| 2011/0153351 A1* | 6/2011 | Vesper | G06Q 10/10 705/2 |
| 2014/0275807 A1* | 9/2014 | Redei | A61B 5/0022 600/300 |

OTHER PUBLICATIONS

Kushida, C. A., Nichols, D. A., Jadmicek, R., Miller, R., Walsh, J. K., & Griffin, K (2012). Strategies for due-identification and anonymization of electronic health record data for use in multicenter research studies. Medical care, 50, S82-S101.

Friedlin, F. J., & McDonald, C. J. (2008). A software tool for removing patient identifying information from clinical documents. Journal of American Medical Informatics Association, 15(5), 601-610.

* cited by examiner

RESEARCH PICTURE ARCHIVING COMMUNICATIONS SYSTEM

PRIORITY CLAIM

This application claims benefit from International Application No. PCT/CA2014/000482, filed Jun. 3, 2014, which in turn claims priority to U.S. Provisional Patent Application having Ser. No. 61/830,871, filed on Jun. 4, 2013, both of which are incorporated herein by reference in their entireties.

FIELD OF THE INVENTION

The present invention relates generally to medical diagnostic imaging systems, and more particularly to medical diagnostic imaging systems that facilitate the removal of personal information from the image data to permit the data to be used in a research environment.

BACKGROUND OF THE INVENTION

Medical images of a patient's body are generally taken by a technician using an imaging modality, such as an x-ray machine or a magnetic resonance (MR) imaging device. At a single imaging session, one or more diagnostic images of one or more body parts may be taken and recorded. Such diagnostic images may then be entered into a picture archiving and communication system (PACS) for later access by a medical practitioner. PACS systems generally store and transmit data in accordance with the Digital Imaging and Communications in Medicine (DICOM) international standard. Imaging modalities, such as MR and other diagnostic imaging devices, generally communicate directly with the PACS over a network using DICOM. The function of the PACS is to maintain a database of diagnostic images taken on connected devices along with related information for image display and patient demographics.

In addition to the image data, the DICOM records include demographic information such as patient identification information, accession number, the start and end times of tests, and may include identification of the attending staff member(s). Privacy concerns, including laws, regulations and institutional policies, strictly limit access to such personally identifiable information so that generally only specifically authorized medical personnel within a medical facility can access such image data with associated DICOM records.

Often research teams in, for example, universities, teaching hospitals, companies performing research and development into new technologies, and pharmaceuticals companies would like to access PACS clinical data in order to perform research studies. However, privacy issues make it difficult to transport PACS data out of the clinical arena due to privacy regulations and rules. To do so requires largely a manual process of de-identifying the data set which is a costly and error-prone endeavour especially when the data sets involved are fairly large, e.g. more than 1000 images per study.

Once the data sets are de-identified, there is no standard way of mapping the fictitious identity back to the original identity so that longitudinal or multi-timepoint studies can be done. Also, once the data sets are de-identified, there is no standard way of transporting the data sets out of the clinical setting in an efficient and secure way Very mature research teams may use a PACS purchased from a traditional clinical PACS vendor to store their research images. Such PACS systems are underpowered because they must adhere to the DICOM data model with Patient-Study-Series entities at the root. Thus, the ability to organize data sets in ways that make the most sense for any particular research project does not exist; one must conform to the DICOM data model. Because of the DICOM data model and the standard for searching, your ability to search for data of relevance is limited in most cases to a Patient or Study identifier. Once many data sets have been stored in the PACS, it is very difficult to make use of this data again, because it is difficult to find the data that would be of interest to the researcher. Once in a traditional clinical PACS, it is also very difficult to retrieve the data in a programmatic way. The DICOM standard assumes an interactive user interface for searches and retrieves. Programmatic and automated retrieval is desirable for research teams because they will often want to retrieve data, run particular processing or analysis algorithms on the data, and then send the output data back into the data store.

Use of a traditional clinical PACS is also problematic in research because such archives will only store DICOM-formatted data, usually with limited support for arbitrarily formatted data files, which is the case with almost all instances of data output from processing or analysis operations.

The use of a traditional clinical PACS does not provide a unified product and tools development platform which leads to a great deal of waste in redundant efforts. For example, at the SPIE Medical Imaging conference held in February 2013, multiple papers were presented that documented projects involving novel image processing or analysis approaches and algorithms all requiring an image viewer of some kind. Every project produced their own, ad hoc image viewer software, even projects from within the same academic institution.

SUMMARY OF THE INVENTION

The following presents a simplified summary of the disclosure in order to provide a basic understanding to the reader. This summary is not an extensive overview of the disclosure and it does not necessarily identify key/critical elements of the invention or delineate the scope of the invention. Its sole purpose is to present some concepts disclosed herein in a simplified form as a prelude to the more detailed description that is presented later.

The present invention provides a research picture archiving and communication system including a clinical subsystem, a de-identified image database, and a de-identification subsystem. The clinical subsystem is in electronic communication with a clinical picture archiving and communication system (PACS). The PACS contains stored image data consisting of images and metadata associated with each image. The image data includes personal information, otherwise known as personally identifiable information. The clinical subsystem is configured to retrieve image data from the PACS. The clinical subsystem includes an image data editor for de-identifying image data by deleting or altering the personal information in the image data according to instructions specified in a de-identification script. The de-identified image database is in electronic communication with the clinical subsystem. The de-identified image database stores de-identified image data. The de-identification subsystem is in electronic communication with the clinical subsystem. The de-identification subsystem includes an image metadata database and runs an edit script generator that can be used by a user to generate a de-identification script based on metadata stored in the image metadata database, without access to the associated image data.

The system may be configured so that user may cause de-identified image data to be stored in the de-identified image database by performing a number of steps using the system. First, the user may instruct the clinical subsystem to extract some of the metadata contained in image data stored in the PACS, and store the metadata in the image metadata database. This may be done via a remote or local workstation. The instruction may be provided indirectly via software running on the de-identification subsystem. Second, the user may use the edit script generator to generate a de-identification script based on the metadata in the image metadata database. Third, the user may provide (by instructing the de-identification subsystem to provide) the de-identification script to the clinical subsystem. Fourth, the user may instruct the clinical subsystem to run the de-identification script on the image data to produce de-identified image data. Fifth, the user may instruct the clinical subsystem to store the de-identified image data in the de-identified image database.

The de-identification subsystem and de-identified image database may be co-located and may both be remote from the clinical subsystem.

The clinical subsystem and PACS may be in secure electronic communication with each other, and the system may ensure that no image data containing images is (non-transitorily) stored in the de-identification subsystem or in the de-identified image database unless the image data has been de-identified.

The de-identification subsystem may further comprise a metadata editor configured to run a de-identification script on metadata in the image metadata database and provide the results (for example, by a visual representation on a workstation screen) to the clinical gatekeeper.

The metadata editor may be further configured to provide to the clinical gatekeeper a comparison of the metadata before and after application of the de-identification script to the metadata.

The system may further include a second clinical subsystem in electronic communication with a second PACS. As with the first PACS, the second PACS has image data stored in it, including images and metadata associated with each image, and the image data includes personal information. The second clinical subsystem is also configured to retrieve image data from the second PACS, and the second clinical subsystem also includes an image data editor for de-identifying image data by deleting or altering the personal information in the image data according to instructions specified in a de-identification script. The system may include additional clinical subsystems in electronic communication with additional PACSs.

DETAILED DESCRIPTION OF THE INVENTION

The RPACS is designed to be used in all contexts that involve the storage, cataloguing, manipulation, processing and distribution of medical images, metadata and ancillary data. Examples of such contexts are research teams that:
- conduct research projects to produce novel image processing and data manipulation tools, such as new image segmentation algorithms;
- are developing novel imaging modalities, such as magnetic resonance imaging enhancements;
- are developing new imaging protocols, such as specific protocols for surgical planning;
- are developing new imaging agents, such as new contrast agents; and
- are conducting clinical trials on new pharmaceuticals and are using medical imaging with biomarkers as endpoints.

The invention is a Research PACS ("RPACS"), which is a hardware and software system including a server machine, and one or more client machines. Data can be input into RPACS, for example, by (i) sending DICOM formatted data using DICOM networking protocols, (ii) uploading an arbitrary binary stream using a web interface to the server; or (iii) programmatically uploading data using the server REST API.

The RPACS server includes separate staging and archive areas, or subsystems. Received data is first stored in the de-identification subsystem where it is de-identified prior to be transferred to the archive area. The presence of a particular flag in the DICOM header indicates whether or not the data has been de-identified.

De-identification

In order to migrate a piece of data from the de-identification subsystem to the archive area, a minimum set of de-identification operations must take place, including the obfuscation of the Patient ID, Patient Name, Study, DICOM Series and Service-Object Pair (SOP) Instance UIDs (Unique Identifiers). The RPACS may also provide for more sophisticated de-identification operations that can be performed via a scripting language.

In general, there are two key actors who use the RPACS, which are the clinical gatekeeper and the researcher. It is generally the responsibility of the clinical gatekeeper to ensure that any data that leaves the clinical environment (clinical subsystem) is properly de-identified. The researcher, on the other hand, needs to check the de-identified data to ensure that the obfuscation process was not so aggressive as to obliterate data that is scientifically relevant to the research project. The clinical gatekeeper and the researcher may be the same person, but generally are different persons.

The process of de-identifying data for transport out of the clinical setting is generally iterative, involving the following steps.
1. Clinical gatekeeper inputs a data set into the de-identification subsystem.
2. clinical gatekeeper creates a de-identification script that will be applied to the data set. a minimum de-identification operation is always performed to prevent data being stored in the archive area that still retains patient health information.
3. The clinical gatekeeper uses a comparison tool that provides a visual representation of the data set pre- and post-de-identification so that correctness can be verified.
4. Once the clinical gatekeeper is satisfied that the script is correct, the clinical gatekeeper moves the data set from the de-identification subsystem to the archive area. the act of moving this data applies the de-identification script.

5. From the de-identification subsystem, the data set can be published to the archive parititon, and access rights granted to the researcher.
6. The researcher logs into the system, only having access rights to those data sets that have been published to them on the archive partition.
7. The researcher will review the de-identified data set to verify that all scientifically relevant data is intact. if so, the process ends. if not, the researcher will notify the clinical gatekeeper and the clinical gatekeeper will modify the de-identification script to correct the problem.
8. Steps 3-7 are repeated.

Once the de-identification script has been verified as performing the correct operation, it can be applied in an automated way as part of an automation rule.

A clinical gatekeeper may apply de-identification operations in an ad-hoc manner to images that reside in the de-identification subsystem when the operations are not intended to be used in automated batch processing situations. The operation can still be previewed by the user, and then is merely applied. No script is stored for re-use nor incorporated into an automation process.

Personal Data in the Image Pixel Map

In some cases, there may be personal information imprinted into an image pixel map (or "pixmap") itself, rather than such information being limited to the image's metadata. This may be done, for example, by OR'ing a pixmap representing the personal information into a portion of the image, the values of the pixels representing the personal information being selected to contrast with the content of the image over which they are laid.

In such cases, the de-identification operation may involve the Clinical Gatekeeper specifying a bounding rectangle for which a solid fill will be applied in order to obfuscate the information.

In cases where the identifying information is automatically generated by the source machine, the location of the information is consistent in all the images of a particular study. An example is ultrasound studies, where the patient's identifying information is included as part of the image bitmap but where this information is rendered in a consistent location time after time. In these cases, the system applies the solid fill in an automated fashion.

In cases where the identifying information may be at different locations in an image, from image to image, automated processing may still be performed by the system. An example of this is when a DICOM image is created as a product of digitizing an analog film image, where the patient information naturally becomes a part of the pixmap. In these cases, the patient's name, date of birth and other identifying information is actually available in the DICOM header. This can be used by the system to apply an OCR algorithm to locate the identifying data in the bitmap and programmatically create a bounding box for a solid fill.

A more generalized OCR algorithm may be applied by the system to the pixmap to locate instances where identifying information is suspected, using a predefined dictionary of names and terms.

An example of a suitable approach to de-identification, or anonymization, of text embedded in imagery can be found in the paper "Automatic Selective Removal of Embedded Patient Information From Image Content of DICOM Files" by Gary Kin-wai Tsui and Tao Chan, in the American Journal of Roentgenology, April 2012, vol. 198, no. 4, pp. 769-772, published by the American Roentgen Ray Society.

QC Option for Automated De-Identification Workflow

A fully automated approach creates the risk in that the system may fail to obfuscate patient identifying data completely. As a safety mechanism, the automation system may optionally allow instances of de-identification to be put into a worklist for review by a human reviewer, to ensure that nothing has been missed. This picking of instances for review can be tuned to range from all instances, to intervals, to random intervals. The instances can also be defined to be one image from a study, one image from one series within a study, all images within a study, or something in between.

Obfuscation of Skin Tissue Data to Prevent Reconstruction of Patient's Face

Image data sets that contain spatial information, such as those in CT and MR imaging, allow 3D reconstruction and rendering to be applied. When this occurs, it's possible to shade the skin surface of such a reconstruction to reproduce the original patient's face in cases where the patient's head was part of the original scan. This obviously creates a potential privacy breach.

The de-identification workflow can optionally include a defacing algorithm whereby the combination of thresholding and distance from air, and distance from a well-known reference point in the patient's body is used to identify voxels representing skin tissue. To accomplish defacing, a localized group of voxels' intensities may be averaged and applied to the same region, and its surface normal may be randomly altered to a small degree. Alternatively, to accomplish defacing, these pixels and their neighbours may be altered so that, rather than forming a smooth contour representing skin tissue, a series of connected, but straight lines are used. Specifically, the skin pixels are identified and then a quantization filter is applied, resulting in a step-like representation. The resulting reconstructed face will take on an appearance of 2D pixelization, censoring results, while important clinical data in tissue other than skin are preserved.

Virtual File System for Image Data Organization

A Virtual File System is a part of the RPACS. This VFS has the following characteristics:

Allows the users to create an arbitrary hierarchical system for organizing image data, down to the DICOM Study level.

The Study-Series-SOP hierarchy needs to be enforced at the branches of the file system tree in order for image data sets to be exportable from the VFS using the DICOM standard.

Above the Study level, however, the hierarchy can be anything the user desires, and manipulation may only require manipulating a conventional operating system's file system. Rather, manipulation is as simple as if the user were manipulating a conventional operating system's file system, with operations such as move, copy, delete. The user interface, however, is embedded within a browser-based web application, so it would not be accessible from the desktop directly.

Any object in the VFS can have one or more tags applied to it, and subsequently, VFS filters can be applied to locate objects that have that tag attached.

The VFS can support a file object of any arbitrary format, in addition to DICOM-formatted objects. Non-DICOM objects are internally encapsulated as a DICOM Raw Data object.

DICOM objects can be rendered using a built-in web-based DICOM viewer.

Non-DICOM objects can be rendered using any associated applications on a particular user's PC, or using the built-in renderer provided by the RPACS system.

Modifications to file objects are audited.

File objects are versioned. Previous versions can be examined.

Metadata on the file and folder objects can be created and built into the RPACS VFS.

A REST API can be used to access, manipulate and download the objects in the VFS. This API can be used a part image processing and analysis pipelines custom built by a user.

Searchability

In addition to a filter-based quick search method, users can also search for contents in the VFS using text-based and other indices.

The data that is indexed includes:

DICOM header data, e.g. Modality, Manufacturer, SOP class;

Full-text indexing on HL7 Order Update messages that contain radiology reports;

Full-text indexing on HL7 Order messages that contain text for Indications;

Terminology and synonym indexing based on natural language processing of the radiology report and indications; and User-defined indexer to be supplied as a plug-in assembly.

Web Distribution of Newly Developed Imaging Tools

Image analysis, manipulation and processing tools that can be accessed via the RPACS Workstation application can be made accessible via a web-based viewer application, CleomeCast, by copying the plug-in assembly onto the server. No additional programming is necessary. This is accomplished through the web-based viewer application using server-side rendering, i.e. interactions with images are actually occurring on the server, and merely the results streamed as images to the client browser.

Cloud Transport and Data Brokering

The transport of images between different institutions is traditionally difficult. Healthcare institutions typically have strong firewall policies and require substantial bureaucratic procedures to be followed before permitting connections to outside institutions in order to protect patient confidentiality.

To ease research collaboration between different institutions involving the sharing of images, the RPACS can connect to the RPACS Network, a transport mechanism that uses standard web-based strong encryption and HTTP transport to facilitate the sharing of image data sets that have already been de-identified, i.e. only those objects in the archive area. This side-steps the need to open ports in the firewall for traditional DICOM-based transport.

Using the RPACS Network, institutions can further publicize the image data that they have available, effectively marketing their intellectual property to others. The RPACS Network then becomes a brokerage for accesses to data, where the operator of the network may make money through brokerage fees.

RPACS Operation

Figure 1:
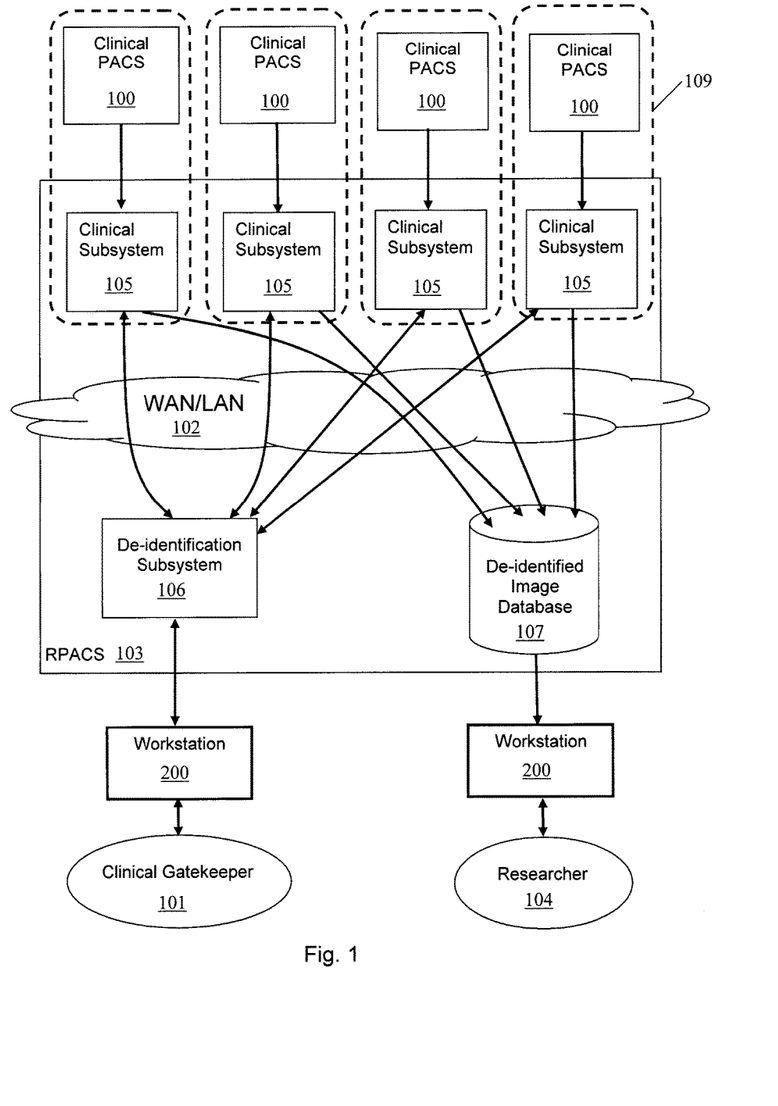
FIG. 1 is a block diagram of the key elements of one embodiment of the RPACS including four clinical subsystems.

FIG. 1 is a block diagram depicting an RPACS 103 including four clinical subsystems 105. In other embodiments there could be any number of clinical subsystems 105 in one RPACS 103. The clinical subsystems 105 are generally located within a hospital 109, or other physical clinical facility, where they communicate with one or more clinical PACSs 100 via a local secure network that is generally behind a firewall and where access is limited to authorized hospital staff. Such a clinical PACS 100 is typically based on the DICOM standard and contains diagnostic images that include, either in the DICOM header or in the image pixmap (i.e. the pixel values that constitute the image), personally identifiable information (or just "personal information") about individuals, such as their names and birth dates. Personally identifiable information generally means information that can be used on its own or with other information to identify, contact, or locate a single person, or to identify an individual in context.

Each clinical subsystem 105 communicates with a de-identification subsystem 106, and also provides de-identified, or anonymized, image data to a de-identified image database 107.

A clinical gatekeeper 101, via the de-identification subsystem 106, can access image metadata from study data retrieved from a PACS 100, construct and test de-identification scripts to de-identify, or anonymize, image data, and send instructions, which may be referred to as a "data contract" or a "de-identification script", to the associated clinical subsystem 105, instruct the clinical subsystem 105 how to process study data in the PACS 100 so as to de-identify it, following which the clinical subsystem 105 transmits the de-identified image data to the de-identified image database 107. The de-identified image data may then be accessed by researchers 104, who would otherwise be prohibited from accessing the image data based on privacy restrictions.

The de-identification subsystem and de-identified image database may be co-located in a hospital 109 (or other clinical facility) and communicate with the local clinical subsystem 105 via the hospital local area network (LAN), and communicate with other clinical subsystems 105 via a wide area network (WAN), such as the internet, This may be done over a secure link, such as a virtual private network (VPN) link. The system is designed so that no image data is ever stored the de-identification subsystem or the de-identified image database in association with any personal information.

Figure 2:
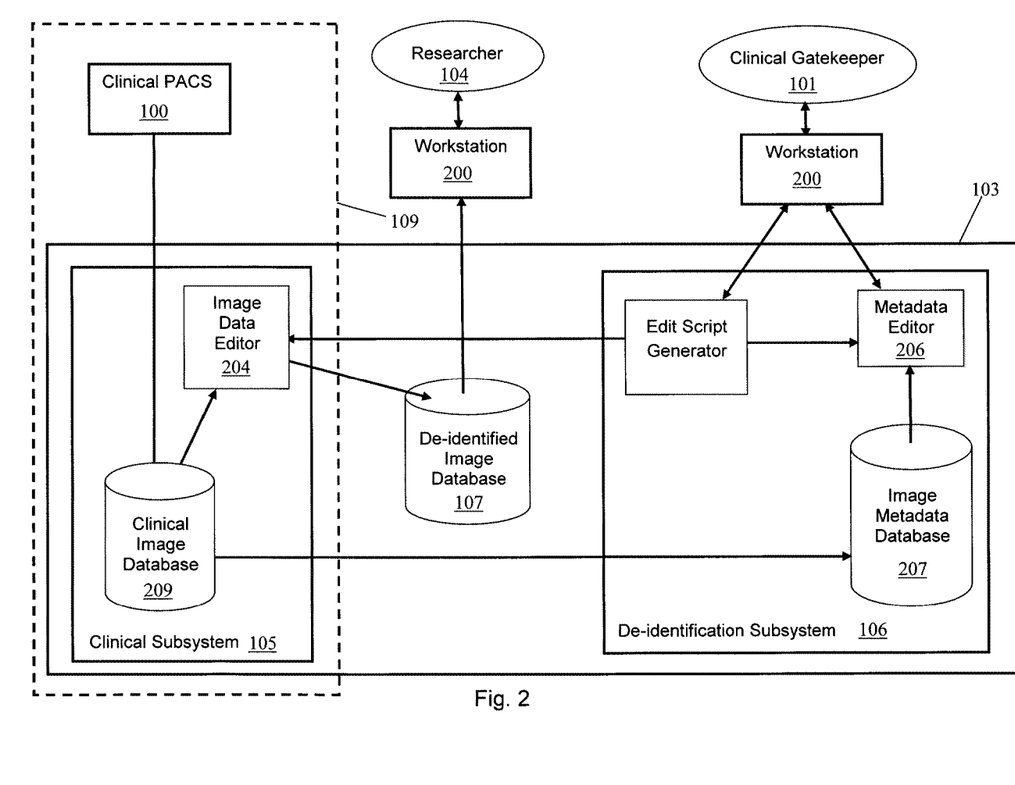
FIG. 2 is a block diagram of the key elements of one embodiment of the RPACS including one clinical subsystem and showing more detail regarding the clinical subsystem and de-identification subsystem.

FIG. 2 shows more detail for an RPACS 103 with a single clinical subsystem 105, which may be co-located with the PACS 100 in a hospital 109. Image data is stored in the clinical subsystem 105 in a clinical image database 209. Input study data sets are retrieved from local hospital PACSs over the hospital LAN. Such data input sets are generally DICOM-formatted data sent using DICOM networking protocols. The clinical subsystem 105 also includes an image data editor 204 that is designed and configured to receive de-identification scripts from the de-identification subsystem 106 portion of the RPACS server 108. A de-identification script is generally a script that instructs the editor as to how to de-indentify all the images in a data set or study. The editor applies the script to the actual clinical data to produce de-identified image data, which it transmits to be stored in the de-identified image database 107.

The de-identification subsystem 106 provides tools for a clinical gatekeeper 101 to examine clinical image data and to develop scripts to de-identify the clinical data.

In a typical operation, a clinical gatekeeper 101 will instruct the clinical subsystem 105 to retrieve a clinical data set for a study from the PACS 100 and store it in the clinical image database 209. The clinical gatekeeper 101 may then instruct the clinical subsystem 105 to retrieve metadata from the DICOM images in that image data and store the metadata in an image metadata database 207 in the de-identification subsystem 106. This data generally includes personal information, but not in association with the related images, which are retained in the clinical subsystem 105 and/or PACS 100. The clinical gatekeeper 101 can then use the edit script generator 208 and metadata editor 206 in the de-identification subsystem 106 to produce a script to edit the metadata to de-identify it. For example, such scripts may replace patient names with pseudonyms or numbers, and replace birth dates with dates that are some random number of days before or after the actual birth date.

Note that it is not essential that an entire clinical data set be copied into the clinical image database 209. In some embodiments, the data may just be retrieved from the PACS 100 as it is required for processing.

The de-identification script may be developed in any suitable language, such as C# or Python using the edit script generator 208. At any point in the development, the clinical gatekeeper 101 may execute a "preview" whereby the metadata editor 206 runs the script on the metadata in the image metadata database 207. This allows the clinical gatekeeper 101 to preview the result of the de-identification using the metadata editor 206 which may display a visual representation of the metadata pre- and post-de-identification. The clinical gatekeeper 101 may repeat this several times as the script is developed until the clinical gatekeeper 101 is satisfied that the script is performing as desired.

At that point, when the clinical gatekeeper 101 is satisfied with the script's performance, the clinical gatekeeper 101 can instruct the edit script generator 208 to send the de-identification script to the image data editor 204 in the clinical subsystem 105. The image data editor 204 then runs the script on the image data in the clinical image database 209 to produce de-identified image data (typically for a study) which is then stored in the de-identified image database 107 where it is accessible to researchers 104. Access privileges for particular researchers 104 to particular data sets in the de-identified image database 107 can be specified by the clinical gatekeeper 101 to limit access to data.

A primary researcher 104 may review a new de-identified data set in the de-identified image database 107 to verify (1) that the de-identification process has not destroyed scientifically relevant data and (2) that personal information does not remain in the data. If these are not the case, the primary researcher informs the clinical gatekeeper 101 of the identified problem so that the clinical gatekeeper 101 can, as required, delete the data set, modify the de-identification script appropriately and instruct the clinical subsystem 105 to re-send the de-identified data set to the de-identified image database 107. If required, this process may be repeated until the primary researcher finds no further problems, at which point the primary researcher 104, and other authorized researchers, may begin to use the de-identified data for scientific analyses.

Preferably, the clinical gatekeeper 101 accesses the de-identification subsystem 106 via a secure link, such as by being located in the same clinical facility as the de-identification subsystem 106. Since a researcher 104 can only access de-identified data in the de-identified image database 107, the researcher may access such data over the interne. However, it is preferred that the primary researcher who performs the checks described above do so on a secure link, until no further problems are found and the data is made available to use in scientific analyses.

In addition to providing access to a de-identified study via access control lists, the RPACS may also facilitate sharing a study with a collaborator who may not have an account on the RPACS system. This is accomplished simply by selecting the study of interest, and then "share with an outside collaborator". This creates a URL that anyone can use to browse to the study in their browser. By default, the link will work for a fixed period, such as 7 days, but the users may extend that duration. As well, the user can optionally ask the system to create a randomly-generated password that must be supplied. This allows very easy collaboration and sharing of research data without involving administrative staff setting up new accounts, adding to the cost of the use of the system. An outsider collaborator can mark up the images, for example, create a measurement to measure the size of a tumor, and have those measurements captured in a structured form, stored in the RPACS database for data processing purposes, all within their browser.

In cases where the personal information is stored in the image pixmap, upon request of the clinical gatekeeper 101, the clinical subsystem 105 may stream the image data directly to the screen of the workstation 200 being used by the clinical gatekeeper 101 (such a stream is not depicted in FIG. 2). Such image data is never stored in non-volatile memory in the de-identification subsystem 106. The clinical gatekeeper 101 can specify the locations, e.g. within a specified bounding rectangle, in the image that need to be obfuscated, and this information can be included in the de-identification script that is sent to the image data editor 204. When applying the script, the image data editor 204 then obfuscates (e.g. blurs or zeros out) the indicated area in the designated images. In some cases, the clinical gatekeeper 101 may associate the area specification with a single image, or with a series of images, in the de-identification script. Since the de-identification is generally accomplished using a scripting language, it is possible for the de-identification script to include logic to determine whether the obfuscation rectangle should be applied or not. For example, if it is known that a particular manufacturer's ultrasound scanners always output the patient demographics in a particular area, and this area cannot be modified as part of system configuration, then the script can be configured to look for the manufacturer's name in the DICOM header. Similarly, the script can look for well-known or pre-defined descriptors in the DICOM header to determine whether or not a particular bounding rectangle can be used, and more than one bounding rectangle can be defined and persisted.

An "alias table" may be used to map original values to substituted values, whatever value type they may be, such as patient identifier, date of birth, study date, etc. A namespace qualifier is applied so that collisions can be avoided, and so that a mapping that is used in one research project will not be identically used in another project, as this is not generally desirable, e.g. John Smith may be substituted by Subject 10000 in one project, and may be substituted by Subject A2600 in another project. The alias table does not store all the original values of a de-identified object, but rather only those that are necessary for consistency in identification within a project. For example, if a de-identification script removes all "private" tags—those that are not defined by the DICOM standard but can be defined by implementers for their own purposes—the alias table does not record the original values. Enough information is recorded in the alias table to preserve consistency within a project, and to trace the identity of the real patient and original study. This is sufficient to locate the original study should the need arise. The RPACS can optionally encrypt the original data and store it along with the de-identified object. This is optional, as some people or organizations discourage this practice because of the possibility that these objects are long-lived and that eventually improved decryption equipment/algorithms will be able to decrypt this data and reveal patient-identifying information.

In all preferred embodiments, the clinical subsystem 105 and de-identification subsystem 106 each include at least one computer processor that can execute software to, for example, perform the functions of the image data editor 204, edit script generator 208, and metadata editor 206. Although it may not be commercially practical, skilled persons will understand that exactly the same functionality can be provided by hardware alone, without the need for any software at all. The use of software on programmable processors is simply more cost-effective and flexible and so it is the preferred method of implementing the described functionality. However the use of computer processors that can communicate via electronic networks is essential to the invention.

The clinical image database 209, de-identified image database 107 and image metadata database 207 each comprise logical storage devices. The de-identified image database 107 and image metadata database 207 may for example share the same physical hardware such as a hard disk drive or array of hard drives. For example, the de-identified image database 107 and de-identification subsystem 106 may be implemented on a single physical computer workstation with sufficient processing and data storage capacity. Similarly, the image data editor 204 and clinical image database 209 may be implemented on a single physical computer system with sufficient processing and data storage capacity.

Generally, a computer, computer system, subsystem, computing device, client or server, as will be well understood by a person skilled in the art, includes one or more than one computer processor, and may include separate memory, and one or more input and/or output (I/O) devices (or peripherals) that are in electronic communication with the one or more processor(s). The electronic communication may be facilitated by, for example, one or more busses, or other wired or wireless connections. In the case of multiple processors, the processors may be tightly coupled, e.g. by high-speed busses, or loosely coupled, e.g. by being connected by a wide-area network.

A computer processor, or just "processor", is a hardware device for performing digital computations. A programmable processor is adapted to execute software, which is typically stored in a computer-readable memory. Processors are generally semiconductor based microprocessors, in the form of microchips or chip sets. Processors may alternatively be completely implemented in hardware, with hard-wired functionality, or in a hybrid device, such as field-programmable gate arrays or programmable logic arrays. Processors may be general-purpose or special-purpose off-the-shelf commercial products, or customized application-specific integrated circuits (ASICs). Unless otherwise stated, or required in the context, any reference to software running on a programmable processor shall be understood to include purpose-built hardware that implements all the stated software functions completely in hardware.

Multiple computers (also referred to as computer systems, computing devices, clients and servers) may be networked via a computer network, which may also be referred to as an electronic network or an electronic communications network. When they are relatively close together the network may be a local area network (LAN), for example, using Ethernet. When they are remotely located, the network may be a wide area network (WAN), such as the internet, that computers may connect to via a modem, or they may connect to through a LAN that they are directly connected to.

Computer-readable memory, which may also be referred to as a computer-readable medium or a computer-readable storage medium, which terms have identical (equivalent) meanings herein, can include any one or a combination of non-transitory, tangible memory elements, such as random access memory (RAM), which may be DRAM, SRAM, SDRAM, etc., and nonvolatile memory elements, such as a ROM, PROM, FPROM, OTP NVM, EPROM, EEPROM, hard disk drive, solid state disk, magnetic tape, CDROM, DVD, etc.). Memory may employ electronic, magnetic, optical, and/or other technologies, but excludes transitory propagating signals so that all references to computer-readable memory exclude transitory propagating signals. Memory may be distributed such that at least two components are remote from one another, but are still all accessible by one or more processors. A nonvolatile computer-readable memory refers to a computer-readable memory (and equivalent terms) that can retain information stored in the memory when it is not powered. A computer-readable memory is a physical, tangible object that is a composition of matter. The storage of data, which may be computer instructions, or software, in a computer-readable memory physically transforms that computer-readable memory by physically modifying it to store the data or software that can later be read and used to cause a processor to perform the functions specified by the software or to otherwise make the data available for use by the processor. In the case of software, the executable instructions are thereby tangibly embodied on the computer-readable memory. It is the express intent of the inventor that in any claim to a computer-readable memory, the computer-readable memory, being a physical object that has been transformed to record the elements recited as being stored thereon, is an essential element of the claim.

Software may include one or more separate computer programs configured to provide a sequence, or a plurality of sequences, of instructions to one or more processors to cause the processors to perform computations, control other devices, receive input, send output, etc.

It is intended that the invention includes computer-readable memory containing any or all of the software described herein. In particular, the invention includes such software stored on non-volatile computer-readable memory that may be used to distribute or sell embodiments of the invention or parts thereof.

It should be understood that the above-described embodiments of the present invention, particularly, any "preferred" embodiments, are only examples of implementations, merely set forth for a clear understanding of the principles of the invention. Many variations and modifications may be made to the above-described embodiment(s) of the invention as will be evident to those skilled in the art.

Where, in this document, a list of one or more items is prefaced by the expression "such as" or "including", is followed by the abbreviation "etc.", or is prefaced or followed by the expression "for example", or "e.g.", this is done to expressly convey and emphasize that the list is not exhaustive, irrespective of the length of the list. The absence of such an expression, or another similar expression, is in no way intended to imply that a list is exhaustive. Unless otherwise expressly stated or clearly implied, such lists shall be read to include all comparable or equivalent variations of the listed item(s), and alternatives to the item(s), in the list that a skilled person would understand would be suitable for the purpose that the one or more items are listed.

The words "comprises" and "comprising", when used in this specification and the claims, are to used to specify the presence of stated features, elements, integers, steps or components, and do not preclude, nor imply the necessity for, the presence or addition of one or more other features, elements, integers, steps, components or groups thereof.

The scope of the claims that follow is not limited by the embodiments set forth in the description. The claims should be given the broadest purposive construction consistent with the description as a whole.

What is claimed is:

1. A research picture archiving and communication system comprising:
   (a) a first clinical subsystem comprising a hardware processor, wherein the first clinical subsystem is in secure electronic communication via a network with a first clinical picture archiving and communication system (PACS), the first PACS having image data stored therein, wherein the image data comprising images and metadata associated with each image, and personal information is included in image content and the metadata of each image, the first clinical subsystem being configured to receive the image data from the first PACS, and the first clinical subsystem comprising an image data editor for de-identifying the personal information by applying a de-identification script to the image data, thereby deleting or altering the personal information to produce de-identified image data, wherein the de-identification script is configured to replace patient names with pseudonyms or numbers.
   (b) a de-identified image database subsystem comprising a storage device in electronic communication via the network with the first clinical subsystem for storing the de-identified image data, and
   (c) a de-identification subsystem being remote from the first clinical subsystem, the de-identification subsystem comprising a hardware processor, wherein the de-identification subsystem is in electronic communication via the network with the first clinical subsystem, the de-identification subsystem comprising an edit script generator usable by a user to generate the de-identification script based at least on the metadata provided by the first clinical subsystem,
   the de-identification script being developed by the user by repeatedly (i) specifying or modifying the de-identification script, (ii) running the de-identification script on the metadata, and (iii) previewing output de-identified image data, until the user is satisfied that the de-identification script is correct,
   wherein the image data editor of the first clinical subsystem is configured to receive via the network the de-identification script from the de-identification subsystem, apply the de-identification script to the stored image data to produce the de-identified image data, and store the de-identified image data in the storage device of the de-identified image database subsystem, and
   wherein the image content is never stored in the de-identification subsystem or the de-identified image database subsystem.

2. The system of claim 1, wherein the de-identification subsystem and the de-identified image database subsystem are co-located.

3. The system of claim 1, wherein the de-identification subsystem further comprises a metadata editor is further configured to run the de-identification script on the metadata provided by the first clinical subsystem and provide results to the user.

4. The system of claim 3, wherein the metadata editor is further configured to provide to the user a comparison of the metadata before and after application of the de-identification script to the metadata.

5. The system of claim 3, wherein the de-identification subsystem further comprises an image metadata database for storing the metadata provided by the first clinical subsystem.

6. The system of claim 1, wherein the user is a clinical gatekeeper.

7. The system of claim 6, further comprising at least one additional clinical subsystem in secure electronic communication with at least one additional PACS.

8. The system of claim 1, wherein the image data received by the first clinical subsystem from the first PACS is stored in a clinical image database in the first clinical subsystem.

9. The system of claim 1, wherein the first clinical subsystem provides an image to the user's workstation for display, the image being associated with the metadata provided by the first clinical subsystem to the de-identification subsystem.

10. The system of claim 9, wherein the image provided to the user's workstation is not stored in non-volatile memory in the workstation or the de-identification subsystem.

11. The system of claim 1, wherein metadata provided by the first clinical subsystem is stored in an image metadata database in the de-identification subsystem.

12. The system of claim 1, wherein the de-identified image data comprises de-identified metadata produced by the application of the de-identification script to the metadata.

13. The system of claim 1, wherein the de-identification script is configured to remove personal information from the images in the image data, and the de-identified image data comprises de-identified images produced by the application of the de-identification script to the images in the image data.

* * * * *